United States Patent [19]
Shah

[11] Patent Number: 6,020,004
[45] Date of Patent: *Feb. 1, 2000

[54] BIODEGRADABLE MICROPARTICLES FOR THE SUSTAINED DELIVERY OF THERAPEUTIC DRUGS

[75] Inventor: Subodh Shah, Newbury Park, Calif.

[73] Assignee: Amgen Inc., Thousand Oaks, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/843,975

[22] Filed: Apr. 17, 1997

[51] Int. Cl.$^7$ ............................... A61K 9/19; B29B 9/00
[52] U.S. Cl. ...................... 424/501; 424/489; 424/426; 264/5; 428/402
[58] Field of Search ............................ 424/426, 501, 424/489; 428/402; 264/5–6

[56] References Cited

U.S. PATENT DOCUMENTS

| | | |
|---|---|---|
| 4,389,330 | 6/1983 | Tice et al. . |
| 4,675,189 | 6/1987 | Kent et al. . |
| 4,997,651 | 3/1991 | Pool et al. . |
| 5,055,307 | 10/1991 | Tsuru et al. . |
| 5,354,556 | 10/1994 | Sparks et al. . |
| 5,384,124 | 1/1995 | Courteille et al. . |
| 5,540,937 | 7/1996 | Billot et al. . |
| 5,688,530 | 11/1997 | Bodmer et al. . |
| 5,700,486 | 12/1997 | Canal et al. . |

FOREIGN PATENT DOCUMENTS

| | | |
|---|---|---|
| 96113435 | 8/1996 | European Pat. Off. . |
| WO 90/13780 | 11/1990 | WIPO . |
| WO 95/29664 | 11/1995 | WIPO . |

OTHER PUBLICATIONS

F.G. Hutchinson, et al.—1985 "Biodegradable polymers for the sustained release of peptides".
D.L. Wise, Ph.D., et al.—1973 "Polylactic acid as a biodegradable carrier for contraceptive steroids".

*Primary Examiner*—Edward J. Webman
*Attorney, Agent, or Firm*—Craig A. Crandall; Ron K. Levy; Steven M. Odre

[57] ABSTRACT

The present invention relates to improved methods of making polymeric microparticles containing a variety of active ingredients, e.g. protein drugs. In addition, the present invention relates to using the above active protein containing polymeric microparticles to prepare compositions for the sustained delivery of the therapeutics.

23 Claims, 7 Drawing Sheets

------- Leptin in Formulation Buffer

——— Leptin from Microparticles on seventh day of in vitro release

| Lane # | Sample Name |
|---|---|
| 1 | Leptin Standard |
| 2 | Mol. Weight Standards |
| 3 | 2 hrs Release Sample |
| 4 | 24 hrs Release Sample |
| 5 | 68 hrs Release Sample |
| 6 | 92 hrs Release Sample |
| 7 | 116 hrs Release Sample |
| 8 | 140 hrs Release Sample |
| 9 | 168 hrs Release Sample |
| 10 | Mol. Weight Standards |

BIODEGRADABLE MICROPARTICLES FOR THE SUSTAINED DELIVERY OF THERAPEUTIC DRUGS

FIELD OF THE INVENTION

The present invention generally relates to improved methods of making biodegradable polymeric microparticles containing an active ingredient. In addition, the present invention relates to use of said microparticles to prepare compositions for the sustained delivery of therapeutics.

BACKGROUND OF THE INVENTION

Due to recent advances in genetic and cell engineering technologies, proteins known to exhibit various pharmacological actions in vivo are capable of production in large amounts for pharmaceutical applications. Such proteins include erythropoietin (EPO), granulocyte colony-stimulating factor (G-CSF), interferons (alpha, beta, gamma, consensus), tumor necrosis factor binding protein (TNFbp), interleukin-1 receptor antagonist (IL-1ra), brain-derived neurotrophic factor (BDNF), kerantinocyte growth factor (KGF), stem cell factor (SCF), megakaryocyte growth differentiation factor (MGDF), osteoprotegerin (OPG), glial cell line derived neurotrophic factor (GDNF) and obesity protein (OB protein). OB protein may also be referred to herein as leptin.

Because these proteins generally have short in vivo half-lives and negligible oral bioavailability, they are typically administered by frequent injection, thus posing a significant physical burden on the patient and associated administrative costs. As such, there is currently a great deal of interest in developing and evaluating sustained-release formulations. Effective sustained-release formulations can provide a means of controlling blood levels of the active ingredient, and also provide greater efficacy, safety, patient convenience and patient compliance. Unfortunately, the instability of most proteins (e.g. denaturation and loss of bioactivity upon exposure to heat, organic solvents, etc.) has greatly limited the development and evaluation of sustained-release formulations.

Attempts to develop sustained-release formulations have included the use of a variety of biodegradable and non-biodegradable polymer (e.g. poly(lactide-co-glycolide)) microparticles containing the active ingredient (see e.g., Wise et al., *Contraception*, 8:227–234 (1973); and Hutchinson et al., *Biochem. Soc. Trans.*, 13:520–523 (1985)), and a variety of techniques are known by which active agents, e.g. proteins, can be incorporated into polymeric microspheres (see e.g., U.S. Pat. No. 4,675,189 and references cited therein).

One such technique is spray-drying, wherein the polymer and active ingredient are mixed together in a solvent for the polymer, and then the solvent is evaporated by spraying the solution, leaving polymeric droplets containing the active ingredient. For a detailed review of spray drying see e.g. Masters, K., "*Spray Drying Handbooks*" (John Wiley & Sons, eds., New York 1984). Although the spray drying technique has proven useful in certain instances, it still suffers from the fact that biologically active proteins are often denatured due to contact with the organic polymer and solvent, or due to the heat generated during the spray drying processes.

Another technique which can be used to form microspheres is solvent evaporation. Solvent evaporation involves the dissolving of the polymer in an organic solvent which contains either dissolved or dispersed active ingredient. The polymer/active ingredient mixture is then added to an agitated continuous phase which is typically aqueous. Emulsifiers are included in the aqueous phase to stabilize the oil-in-water emulsion. The organic solvent is then evaporated over a period of several hours or more, thereby depositing the polymer around the core material. For a complete review of the solvent evaporation procedure see e.g. U.S. Pat. No. 4,389,330 (and references cited therein). As with the spray drying technique, solvent evaporation techniques have proven useful in certain instances. However, the technique is often not preferred because active ingredient is often lost during the solvent extraction process. This is because the process involves emulsification into an aqueous phase, and a water soluble drug will often rapidly partition from the more hydrophobic polymer-solution phase into the aqueous surroundings.

Yet another technique which can be used to form microspheres is phase separation, which involves the formation of a water-in-oil emulsion or oil in water emulsion. The polymer is precipitated from the continuous phase onto the active agent by a change in temperature, pH, ionic strength or the addition of precipitants. For a review of phase separation techniques, see e.g. U.S. Pat. No. 4,675,800 (and references cited therein). Again, this process suffers primarily from loss of active ingredient due to denaturation.

The release characteristics for the active ingredient from microparticles prepared by methods such as those described above may be continuous or discontinuous, and in some cases, the initial level of active ingredient release is too high or too low. Thus, various additives are often utilized in an attempt to control the release of active ingredient (see e.g., EP 0 761 211 A1, published Mar. 12, 1997).

To avoid the denaturation of protein and other fragile biological molecules which occurs upon spray drying, solvent evaporation or phase separation by classical techniques, the emulsion of polymers and active ingredient can be atomized into frozen nonsolvent overlayed with liquified gas such as nitrogen to form particles, and then extracted at very low temperatures. The extremely low processing temperatures may preserve the activity and integrity of the fragile biological molecules such as proteins. However, the method leads to poor loading efficiencies and yields, resulting in the loss of precious biological material, and is cumbersome, difficult and expensive to implement at the large scales required for commercial production.

Clearly the need still exists for an improved method for preparing polymeric microparticles containing an active ingredient which is simple, inexpensive, versatile, and, most importantly, which protects against loss of protein activity and which provides for high loading efficiencies and yields, thereby allowing for more consistent active ingredient release over an extended period of time.

SUMMARY OF THE INVENTION

As fully described below, the present invention provides an improved method for preparing polymeric microparticles containing an active ingredient through unique utilization of direct lyophilization of emulsion or suspension. This improved method provides several significant advantages over the processes described in the art, including, for example, 1) ease of manufacture of the active ingredient loaded microparticles (i.e. fewer and less cumbersome steps); and 2) the provision of sustained release formulations that maintain the activity and integrity of the active ingredient during release, thus providing for controlled release of active ingredient over an extended period of time.

Additionally, the processes of the present invention provide the advantages of versatility as relates to the class of polymers and/or active ingredient which may be utilized, as well as attainment of higher yields, high loading, and higher loading efficiencies.

Accordingly, one aspect of the present invention relates to a new and improved process for preparing a composition comprising an active ingredient contained within polymeric microparticles, wherein a mixture of the active ingredient and the polymer are dispersed within a continuous phase, the resulting dispersion is frozen, and the water and organic solvents removed from the dispersion by lyophilization. Importantly, the present process is more refined and simpler than those described in the art, and the activity and integrity of the active ingredient is maintained throughout the process.

The present process can be generally described as comprising the steps of: (a) preparing a polymeric solution; (b) adding an active ingredient to produce a mixture; (c) dispersing said mixture within a continuous phase to produce a dispersion; (d) adding an excipient to said dispersion; (e) freezing said dispersion to produce a frozen mixture; and (f) lyophilizing said frozen mixture to produce the desired active ingredient containing microparticles. Alternatively, step (b) can be omitted and "blank" microparticles prepared, onto which active ingredient is then loaded by suspending the blank microparticles in active ingredient solution.

A second aspect of the present invention is a pharmaceutical composition for the sustained-release of an active ingredient comprising a biologically active ingredient contained within polymeric microparticles, or, alternatively, a biologically active ingredient loaded onto the polymeric microparticles. Importantly, the sustained-release compositions of the present invention maintain the activity and integrity of the active ingredient during encapsulation and release, which helps to provide for longer periods of consistent release.

DETAILED DESCRIPTION

Figure 1:
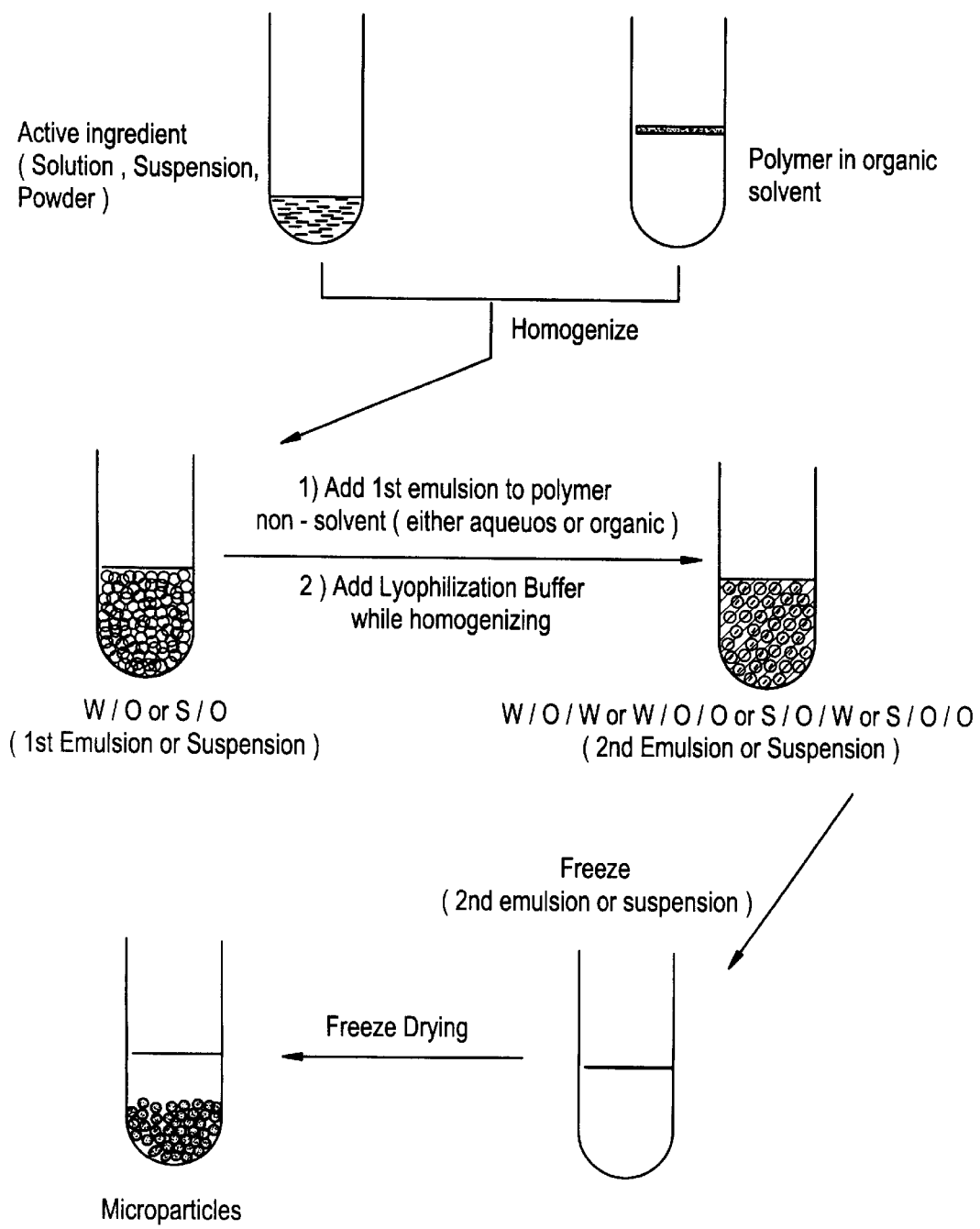
FIG. 1 is a schematic of the process of the present invention for making the active ingredient containing microparticles.

Polymers may be selected from the group consisting of biocompatible and/or biodegradable polymer. As defined herein, biodegradable means that the composition will erode or degrade in vivo to form smaller chemical species. Degradation may occur, for example, by enzymatic, chemical or physical processes. Suitable biodegradable polymers contemplated for use in the present invention include poly (lactide)s, poly(glycolide)s, poly(lactic acid)s, poly(glycolic acid)s, polyanhydrides, polyorthoesters, polyetheresters, polycaprolactone, polyesteramides, polycarbonate, polycyanoacrylate, polyurethanes, polyacrylate, blends and copolymers thereof.

The range of molecular weights contemplated for the polymers to be used in the present processes can be readily determined by a person skilled in the art based upon such factors the desired polymer degradation rate. Typically, the range of molecular weight will be 2000 to 2,000,000 Daltons. Almost any type of polymer can be used provided the appropriate solvent and non-solvent are found.

The term "PLGA " as used herein is intended to refer to a polymer of lactic acid alone, a polymer of glycolic acid alone, a mixture of such polymers, a copolymer of glycolic acid and lactic acid, a mixture of such copolymers, or a mixture of such polymers and copolymers. Preferably, the biodegradable polymer will be poly lactide-co-glycolide (PLGA).

Unless otherwise noted, the term microparticles can be used to encompass microparticles, microspheres, and microcapsules. Active agents to be incorporated into the microparticles are synthetic or natural compounds which demonstrate a biological effect when introduced into a living creature. Contemplated active agents include peptides, small molecules, carbohydrates, nucleic acids, lipids, and proteins. Proteins contemplated for use include potent cytokines, including various hematopoietic factors such as G-CSF, GM-CSF, M-CSF, MGDF, the interferons (alpha, beta, and gamma), interferon consensus, the interleukins (1–12), erythropoietin (EPO), fibroblast growth factor, TNF, TNFbp, IL-1ra, stem cell factor, nerve growth factor, GDNF, BDNF, NT3, platelet-derived growth factor, and tumor growth factor (alpha, beta), osteoprotegerin (OPG), and OB protein.

Also contemplated for incorporation into the compositions of the present invention are derivatives, fusion proteins, conjugates, analogs or modified forms of the natural active ingredients. Chemical modification of biologically active proteins has been found to provide additional advantages under certain circumstances, such as increasing the stability and circulation time of the therapeutic protein and decreasing immunogenicity. For example, U.S. Pat. No. 4,179,337, Davis et al., issued Dec. 18, 1979, discloses conjugation of water-soluble polypeptides such as enzymes and insulin to polyethylene glycol (PEG); see also WO 87/00056, published Jan. 15, 1987.

Another type of chemical modification contemplated for the active ingredients of the present invention is succinylation. The properties of various succinylated proteins are described in Holcenberg et al., *J. Biol. Chem*, 250:4165–4170 (1975), and WO 88/01511 (and references cited therein), published Mar. 10, 1988.

The present OB proteins used are preferably those with amino acid sequence of natural human OB protein; see Zhang et al., *Nature* 3:425–432 (1994); see also, the Correction at *Nature* 374: 479 (1995), optionally with an N-terminal methionyl residue incident to bacterial expression is used. (See, Materials and Methods, infra). PCT publication No. WO 96/05309, published Feb. 22, 1996, entitled, "Modulators of Body Weight, Corresponding Nucleic Acids and Proteins, and Diagnostic and Therapeutic Uses Thereof" fully sets forth OB protein and related compositions and methods, and is herein incorporated by reference. An amino acid sequence for human OB protein is set forth at WO 96/05309 Seq. ID Nos. 4 and 6 (at pages 172 and 174 of that publication), and the first amino acid residue of the mature protein is at position 22 and is a valine residue. The mature protein is 146 residues (or 145 if the glutamine at position 49 is absent, Seq. ID No. 4).

Specific OB protein derivatives contemplated for use in the present invention include Fc-OB protein fusions, succinylated-OB protein, and zinc derivatized OB protein. It is desirable to have such OB protein containing sustained-release compositions as such compositions could serve to enhance the effectiveness of either exogenously administered or endogenous OB protein, or could be used, for example, to reduce or eliminate the need for exogenous OB protein administration.

In general, an aqueous solution, a suspension, or a solid form of the active agent can be admixed with the organic solvent containing the polymer. When an aqueous solution of active ingredient is used, polymer:active ingredient emulsions will be formed and used to prepare microparticles. When a suspension or solid form of active ingredient is used, polymer:active ingredient suspensions are formed and used to prepare the microparticles.

The principal embodiment of the method for making the protein loaded microparticles comprises: (a) dissolving a polymer in an organic solvent to produce a polymeric solution; (b) adding an active ingredient in a form selected from the group consisting of an aqueous solution, a suspension, and a powder to said polymeric solution to produce a active ingredient-polymer mixture comprising a first emulsion or suspension; (c) dispersing said first emulsion or suspension within a continuous phase to produce a dispersion; (d) adding an excipient to said dispersion to produce a final dispersion; (e) freezing said final dispersion; and (f) lyophilizing said frozen final dispersion to remove different solvents (aqueous and organic) to produce the desired protein loaded microparticles. The process is shown schematically in FIG. 1. As depicted in FIG. 1, step c) can alternatively comprise diluting said first emulsion or suspension with a polymer non-solvent. Additionally, step a) can comprise active ingredient being dissolved directly in the organic polymer solution to form a homogeneous first mixture.

The solvent to be used for dissolving the PLGA in step a) of the present processes includes, for example, chloroform, ethyl acetate, methylene chloride, acetonitrile, THF and acetone. In one embodiment of the present invention, the solvent to be used is chloroform. Non-solvents contemplated for use in step c) include water, hexane, ethanol, methanol, and carbon tetrachloride.

The polymer concentrations contemplated for use in the processes of the present invention are in the range of 5–70 gm/100 mL. In the embodiments of the present invention which utilize PLGA, the polymer concentration will preferably be in the range of 10–20 gm/100 mL.

The protein concentrations contemplated for use in the processes of the present invention are in the range of 0–300 mg/mL when in solution or suspension, or equivalent solid protein. In the embodiments of the present invention which utilize OB protein, the protein concentration is preferably 100 mg/mL.

For the emulsions produced in the processes of the present invention, the organic:aqueous ratios contemplated for use are 1:1 to 12:1. In the embodiments of the present invention which utilize PLGA and OB protein, the organic:aqueous ratio will preferably be 4:1 for the first emulsion. In general, the microparticles prepared by the methods of the present invention will generally comprise 0–60% by weight of protein.

The addition of a lyophilization excipient in step d) of the process described above was found to be necessary to insure that the microparticles did not aggregate or fuse during lyophilization. One or more excipients may be added. Importantly, such excipient(s) could also be added in step b) or c) of the process. The lyophilization excipient(s) contemplated for use in the present processes include lactose, mannitol, dextran, sucrose, heparin, glycine, glucose, glutamic acid, gelatin, sorbitol, dextrose, trehalose, methocel, hydroxy ethyl cellulose, hydroxy ethyl starch, poly(ethylene glycol), poly(vinyl pyrolidone) and polyvinyl alcohol, or various combinations thereof, as well as other buffers, protein stabilizers, cryoprotectants, and cyropreservatives commonly used by those skilled in the art.

The temperatures contemplated for use in the freezing step (step e) of the present processes are in the range of −283° C. (liquid nitrogen) to −20° C. These temperatures are utilized so as to stabilize the emulsions or suspensions. The final emulsion or suspension can be frozen immediately using the temperatures described above, or can be stored prior to freezing. In one embodiment of the present invention, the final emulsion was frozen immediately and the temperature utilized for the freezing was −80° C.

The temperatures contemplated for use in step f) of the present processes are in the range of −100° C. to room temperature. Preferably, the temperature of the frozen sample of step e) will be lowered −80° C. and held for one hour prior to being connected to the vacuum system. The temperature is then raised step-wise in 5° C./hour increments to −25° C. to effect removal of the aqueous phase and any residual organic phase. The sample is then held under vacuum for 4–5 days (or whenever the vacuum gauge indicates no more vapor removal), and then the temperature raised to −5° C. for 6–8 hours before the removing the sample from the vacuum system. It is utilization of this single step, i.e., direct lyophilization of the final emulsion or suspension, which refines and simplifies the present process over previously described processes, which require multiple steps and are often cumbersome. And, importantly, this direct lyophilization provides the enhanced stability for a wide variety of active ingredient in vivo, as well as the attainment of higher loading, higher loading efficiencies, and higher yields.

Thus, the significant advantages of the present processes as compared to the processes described in the art, include for example, 1) ease of manufacture of the active ingredient loaded microparticles; 2) versatility as relates to the class of polymers and/or active ingredients which may be utilized; 3) higher yields and loading efficiencies; and 4) the provision of sustained release formulations that release active, intact active ingredient in vivo, thus providing for controlled release of active ingredient over an extended period of time (e.g. up to 180 days). As used herein the phrase "contained within" denotes a method for formulating an active ingredient into a composition useful for controlled release, over an extended period of time of the active ingredient.

In the sustained-release compositions of the present invention, an effective amount of active ingredient will be utilized. As used herein, sustained release refers to the gradual release of active ingredient from the polymer matrix, over an extended period of time. The sustained release can be continuous or discontinuous, linear or non-linear, and this can be accomplished using one or more polymer compositions, drug loadings, selection of excipients, or other modifications.

In general, comprehended by the present invention are pharmaceutical compositions comprising effective amounts of protein or derivative products of the invention together with pharmaceutically acceptable diluents, stabilizers, preservatives, solubilizers, emulsifiers, adjuvants and/or carriers. Such compositions include diluents of various buffer content (e.g., Tris-HCl, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); see, e.g., Remington's Pharmaceutical Sciences, 18th Ed. (1990, Mack Publishing Co., Easton, Pa. 18042) pages 1435–1712 which are herein incorporated by reference. An effective amount of active ingredient is a therapeutically, prophylactically, or diagnostically effective amount, which can be readily determined by a person skilled in the art by taking into consideration such factors as body weight, age, therapeutic or prophylactic or diagnostic goal, and release rate desired.

A suspension of protein loaded microparticles prepared in accordance with the present invention is preferably administered by injection intraperitoneally, subcutantenously, or intramuscularly. However, it would be clear to one skilled in the art that other routes of delivery could also be effectively utilized using the compositions of the present invention.

The following examples are offered to more fully illustrate the invention, but are not to be construed as limiting the scope thereof. Example 1 describes the novel method for preparing protein loaded microparticles. OB protein (in the form of an aqueous solution) is used as an example protein and the ability of OB protein loaded microparticles to provide for sustained release of OB protein, both in vitro and in vivo is demonstrated. Example 2 demonstrates that different polymers can be used to make OB protein loaded microparticles. Example 3 demonstrates that different OB protein derivatives, as well as entirely different proteins (all in the form of an aqueous solution), can be used in the novel methods of the present invention. Example 4 demonstrates the effects of temperature on the freezing step and on the lyophilization step of the process of the present invention. Example 5 demonstrates that different organic solvents can be used to dissolve the PLGA polymers in the methods of the peasant invention. Example 6 demonstrates that a OB protein suspension, Zn/OB protein, can be used in the novel methods of the present invention. Example 7 demonstrates that a spray-dried protein, spray-dried IL-1ra, can be used in the novel methods of the present invention. Example 8 demonstrates that "blank" microparticles onto which active ingredient (e.g. BDNF) has been absorbed, can also provide for sustained release of active ingredient in vitro. Materials and methods follow.

EXAMPLE 1

This example describes the novel method for preparing protein loaded microparticles; specifically, the preparation of poly(D,L-lactide-co-glycolide) microspheres containing OB protein.

0.6 g of RG-502H, poly(D,L-lactide-co-glycolide) (Boehringer Ingelheim Chemicals (B.I. Chemicals), Henley Div., Montvale, N.J.) was dissolved in 4 mL of chloroform and filtered through a 0.2 $\mu$m PTFE filter. 1 mL of OB protein at 100 mg/mL in 10 mM sodium acetate, pH 4.8 (prepared as described in Materials and Methods, infra), was first sterile filtered and then gently added to the top of the polymer solution. The two layers were homogenized using a Polytron homogenizer (PT-DA3012/2T generator, Brinkman, Westbury, N.Y.) at 15,000 to 20,000 rpm for 30–45 seconds while the emulsion container was immersed in an ice bath.

The resultant first emulsion (w/o) was added to 10 mL of water while homogenizing at 15,000 rpm for 20–30 sec. To the resulting second emulsion (w/o/w), 1 mL of lyophilization excipient (100 mg/mL Glycine, 100 mg/mL Sucrose, 10 mg/mL polyvinyl-alcohol (PVA) [22,000 M.W., 88% Hydrolyzed], 10% v/v ethanol) was added and briefly homogenized to insure thorough mixing. The final emulsion under optical microscope showed 1–10 $\mu$m free flowing spheres. The final emulsion was poured into a flask and frozen at −45° C.

The temperature of the bath was then reduced in one hour to −80° C. After an hour at −80° C., the flask was connected to a vacuum system and lyophilization first carried out at −80° C. The vacuum level was monitored so that removal of organic solvent could be determined by a drop in vacuum to the system level. The temperature was then raised step-wise in 5° C./hour increments to −25° C. to effect the removal of the aqueous phase and any residual organic phase.

After 4–5 days when the vacuum gauge indicated no more vapor removal, the temperature of the bath was raised to −5° C. for 6–8 hours before removing the samples from the vacuum system. The microparticles were weighed and then stored at −20° C. until needed.

In vitro Release of OB Protein From PLGA Microrarticles

Figure 2:
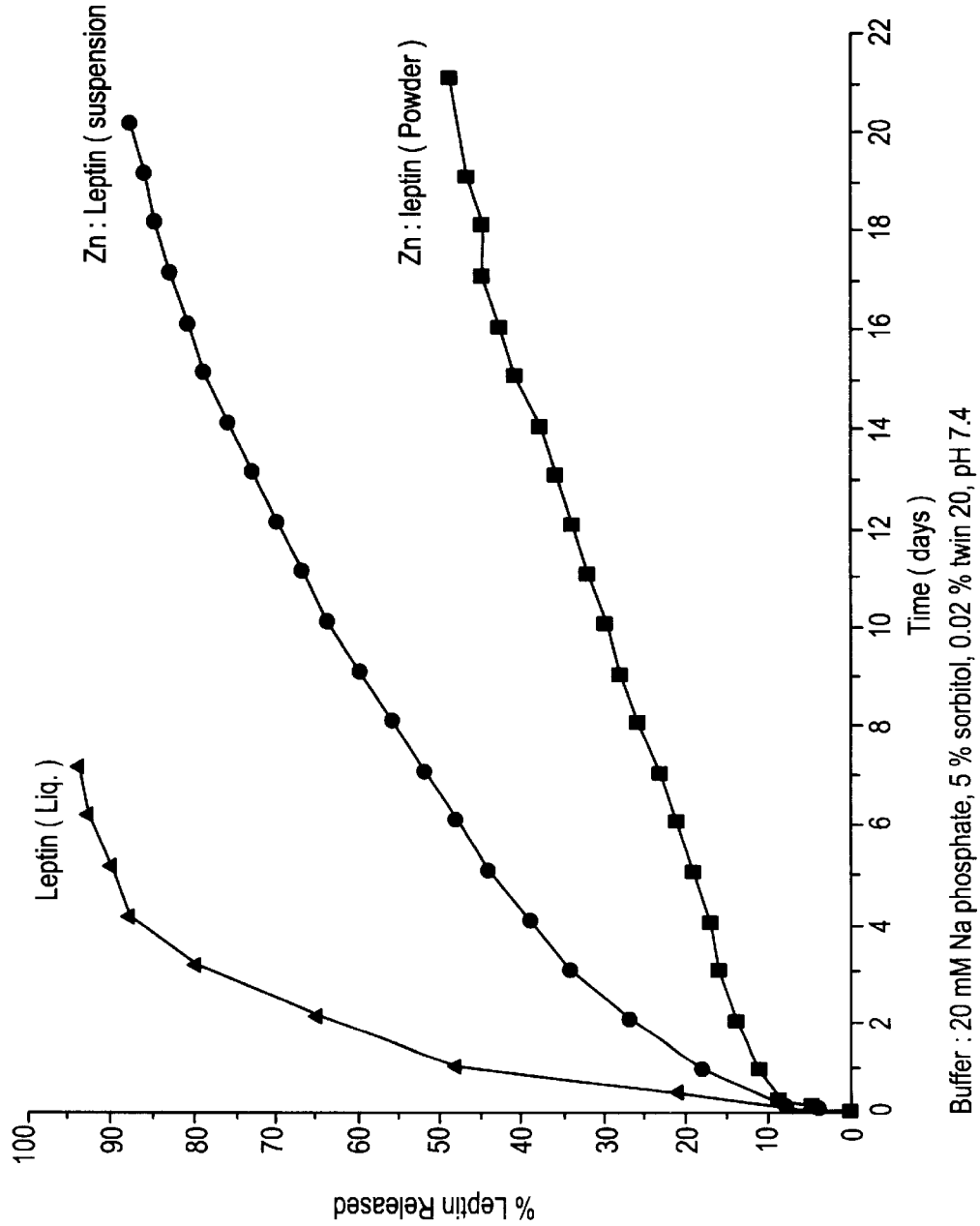
FIG. 2 is a plot depicting the in vitro release of OB protein (leptin) from OB protein loaded microparticles. % OB protein released (OB protein concentration having been determined by UV spectrophotometer at 280 nm) is plotted vs. time (days).
Figure 3:
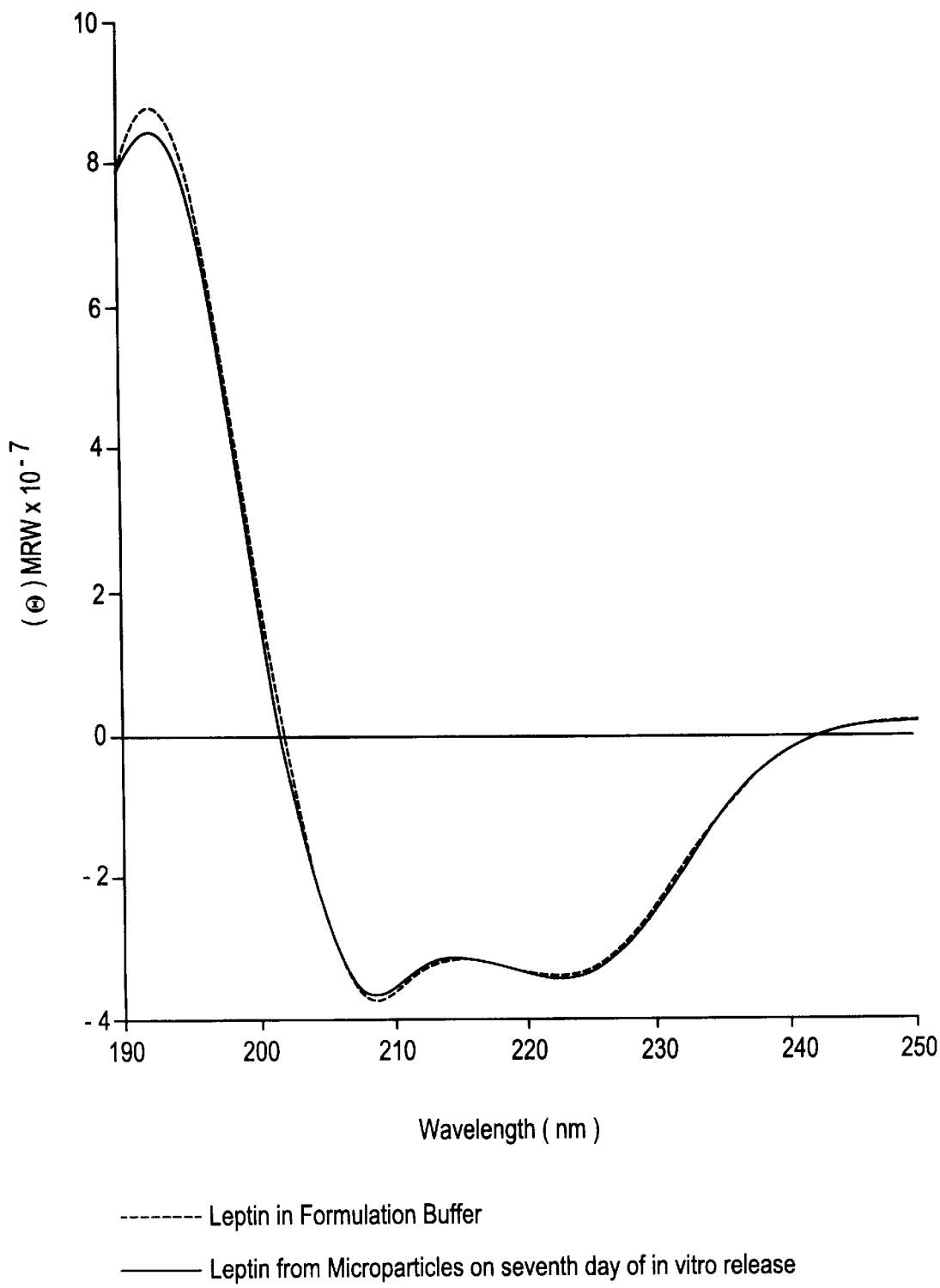
FIG. 3 shows the circular dichroism (CD) data comparing OB protein released from OB protein loaded microparticles (in vitro) on day 7 (solid line) vs. a control sample of OB protein in formulation buffer (dashed line). CD spectra were obtained with a Jasco J-720 spectrapolarimeter (Japan Spectroscopic Co., Tokyo, Japan). The samples (3.5 µM as determined by $A_{280}$) were analyzed at 22° C. with a cell path length of 0.1 cm.
Figure 4:
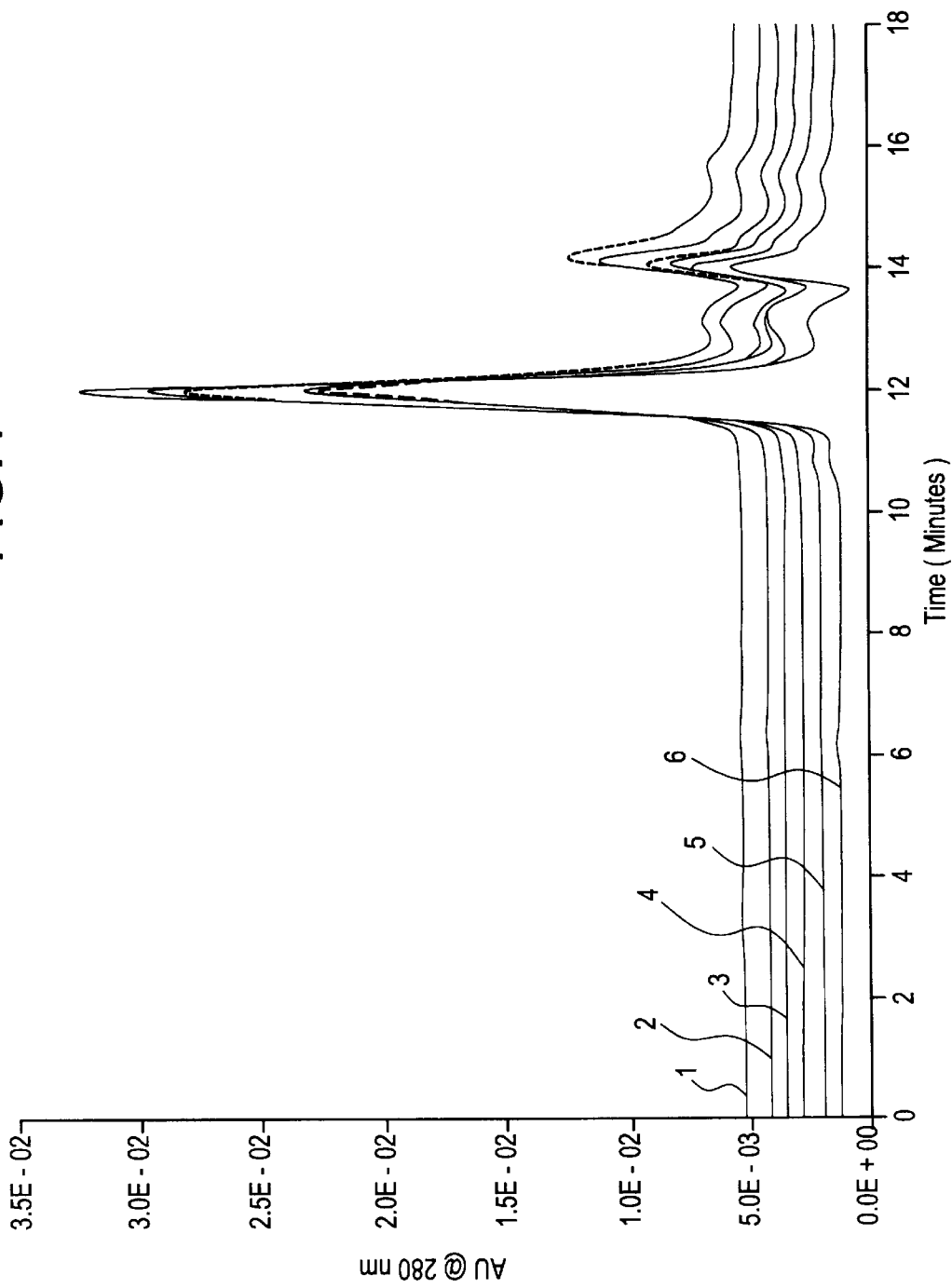
FIG. 4 shows the high performance liquid chromatography (HPLC) data for OB protein released from OB protein loaded microparticles (in vitro) at various time points (0 to 168 hours). Analytical Size Exclusion Chromatography (SEC) was performed with a TosoHaas G2000 SW column (Montgomery, Pa.) using a Waters HPLC (Milford, MA) with 20 mM sodium phosphate, 125 mM NaCl, pH 7.4 at 0.8 mL/min. Absorbance at 280 nm is plotted vs. run time (minutes).
Figure 5:
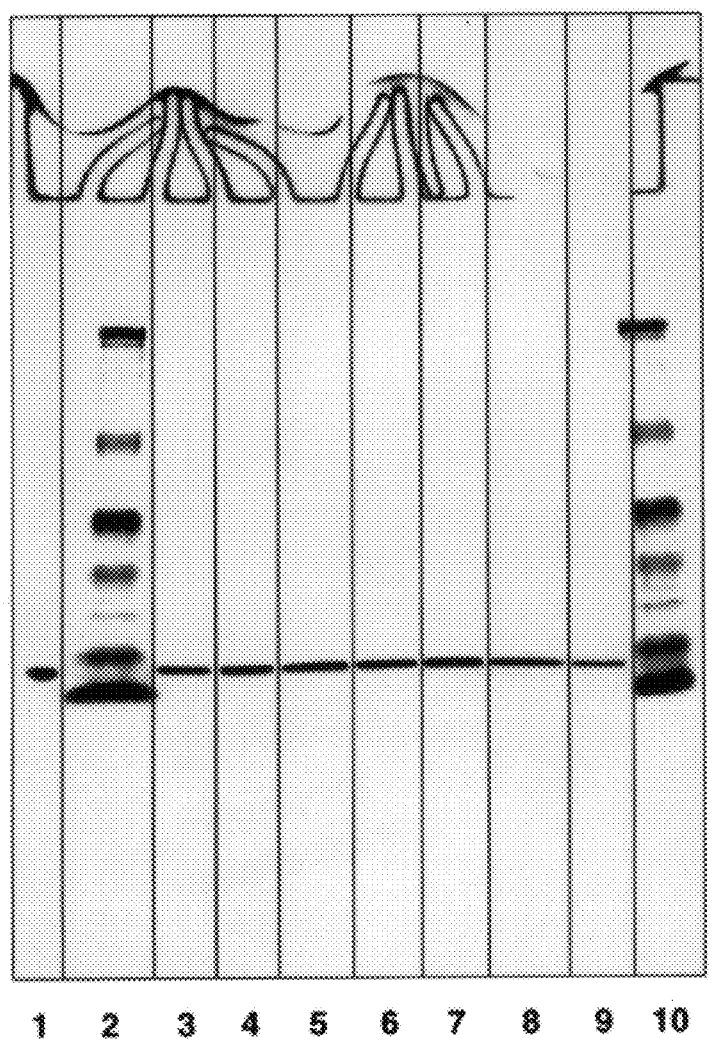
FIG. 5 is a picture of an SDS-PAGE gel (2–20% Trisglycine gel (Novex, San Diego, Calif.)) containing the following samples: lane 1: OB protein standard; lane 2: molecular weight standards; lanes 3–9: OB protein released from OB protein loaded microparticles (in vitro) at 2 hours, 24 hours, 68 hours, 92 hours, 116 hours, 140 hours, and 168 hours, respectively; lane 10, molecular weight standards. Samples were diluted with nonreducing SDS buffer, heated at 100° C. for five minutes and 1 µg of protein loaded into each well. The gels were stained with Coomassie Blue R-250.

"In vitro" release kinetics of OB protein from the microparticles prepared as described above were determined by making a 20 mg/mL suspension of the particles in 20 mM sodium phosphate (or histidine), 5% Sorbitol, pH 7.4. At each time interval, the microsphere suspension was centrifuged and OB protein concentration in the supernatant was determined by UV spectrophotometer at 280 nm as well as by SEC-HPLC at 220 nm. The % OB protein released over time is depicted in FIG. 2. The integrity of the OB protein released from the PLGA microparticles was confirmed by circular dichroism (CD) (FIG. 3), HPLC (FIG. 4), in vitro bioassay and gel electrophoresis (SDS-PAGE) (FIG. 5). The CD data showed retention of secondary structure, and HPLC and gel electrophoresis showed no obvious chemical degradation or aggregation.

In vivo Bioactivity of OB Protein Loaded Microrarticles

Figure 6:
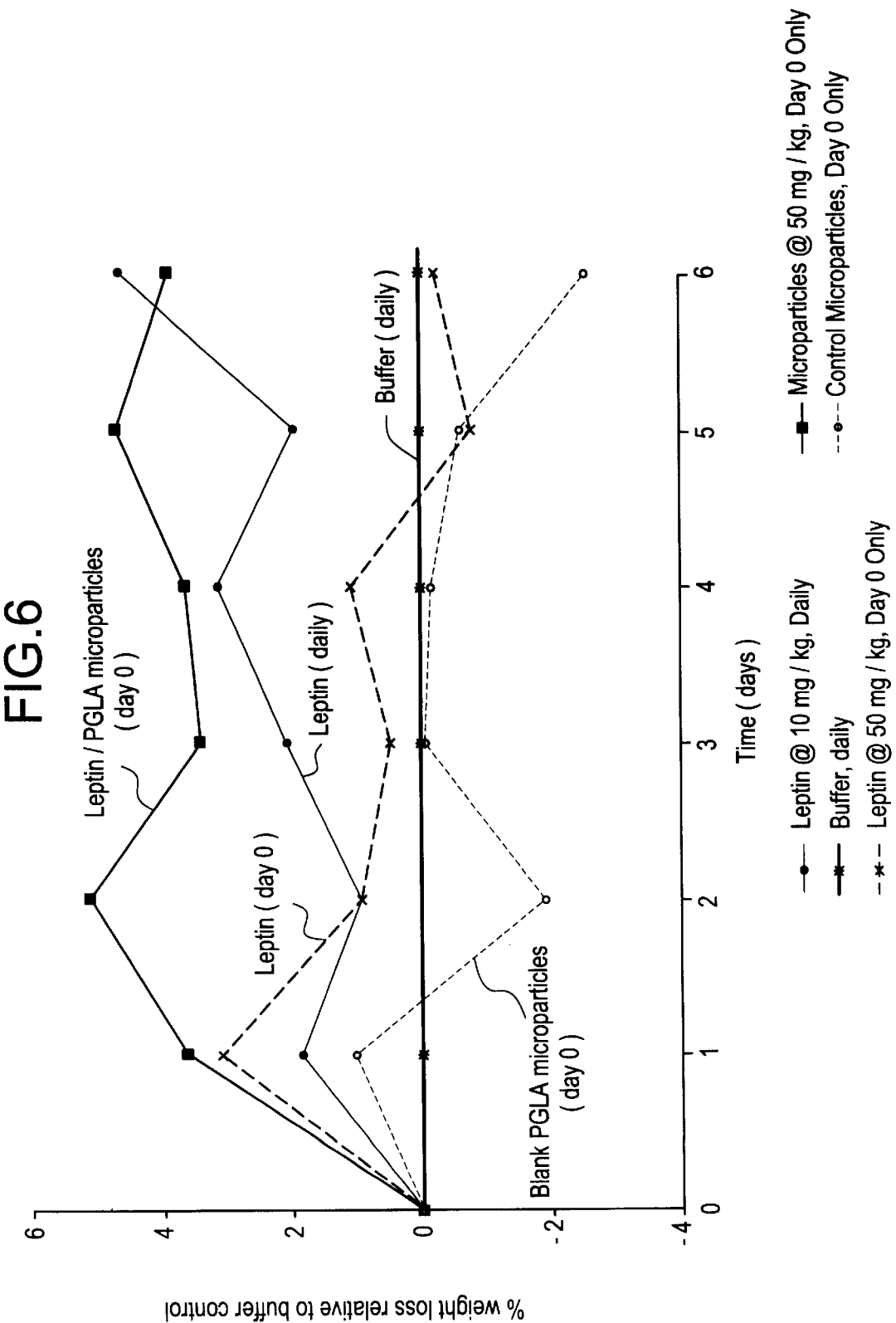
FIG. 6 shows in vivo bioactivity of OB protein (leptin) loaded microparticles in normal mice, in terms of % body weight loss relative to buffer control for a 7 day period. Buffer control (-*-) is plotted vs. leptin injected @ 10 mg/kg daily (-●-) vs. leptin injected @ 50 mg/kg on day 0 only (-x-) vs. leptin loaded microparticles injected @ 50 mg/kg on day 0 only (- -) vs. control microparticles injected on day 0 only (-○-).
Figure 7:
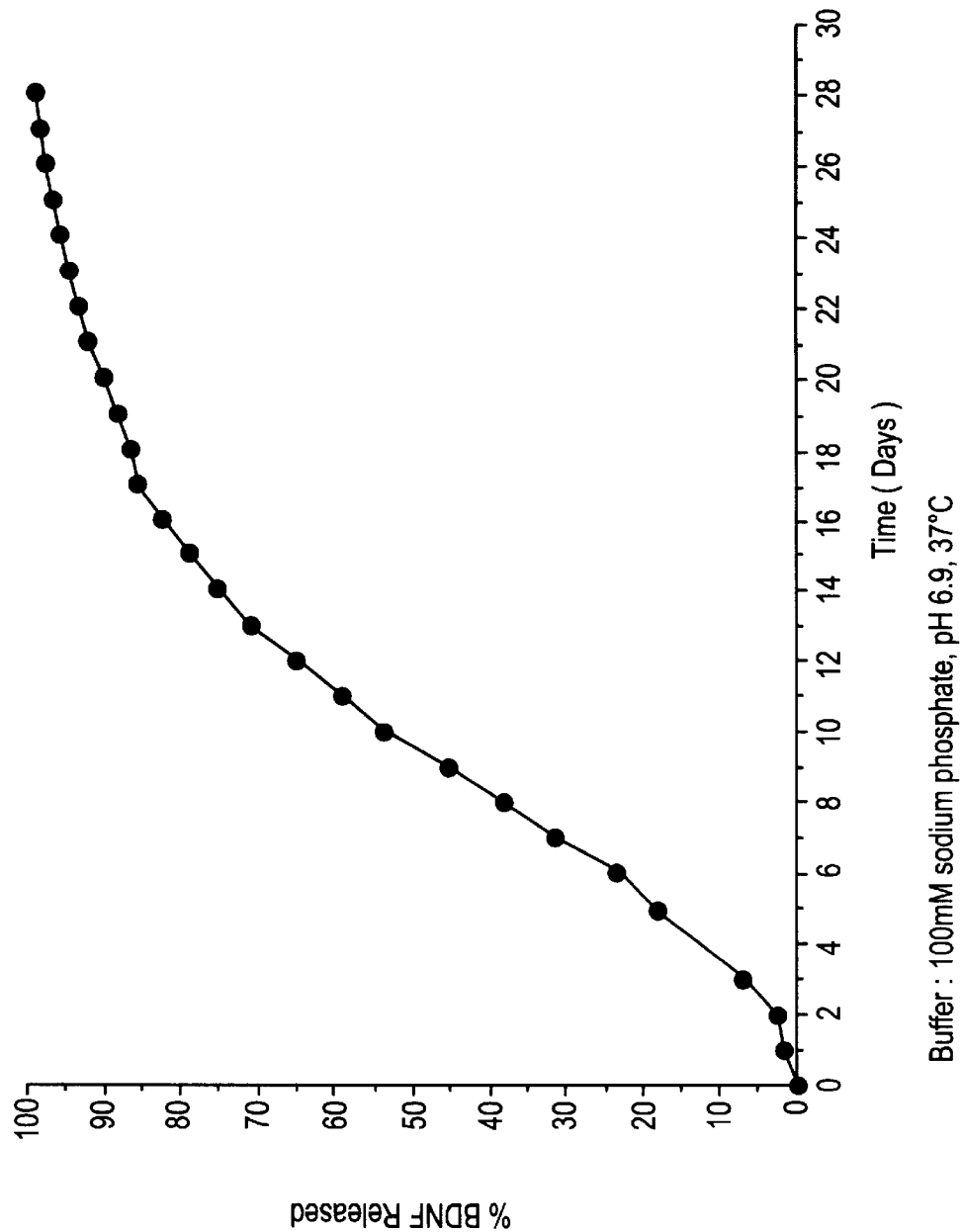
FIG. 7 is a plot depicting the in vitro release of BDNF from microparticles onto which BDNF had been absorbed. % BDNF released (BDNF protein concentration having been determined by UV spectrophotometer at 280 nm) is plotted vs. time (days).

"In vivo" bioactivity of OB protein loaded microparticles were evaluated in normal mice and rats by suspending 80–100 mg/mL microparticles in 20 mM sodium phosphate, 5% Sorbitol, pH 7.4, buffer. The suspensions were prepared an hour before subcutaneous injection by placing the microparticles and buffer on a shaker in a 5° C. cold room. All subsequent manipulations immediately prior to injection were done with refrigerated syringes and 25-gauge needles. % body weight loss relative to buffer control was determined for a 7 day period. After day 7, animals were sacrificed for histological examination of the injection site. A single injection of OB protein loaded microparticles resulted in sustained weight loss in mice for 7 days period (FIG. 6). Histological examination of the injection site revealed a localized minimal to mild inflammatory reaction, which was fully reversible with biodegradation of the microparticles over time.

EXAMPLE 2

This example was designed to test the effectiveness of different molecular weights of PLGA or blends in the preparation of OB protein loaded microparticles. The preparation and evaluation procedures described in Example 1 were utilized to test the various polymers listed in Table 2 below.

TABLE 2

| Polymers: | Source: |
| --- | --- |
| RG-501H | B. I. Chemicals |
| RG-502H | B. I. Chemicals |
| RG-502 | B. I. Cheinicals |
| RG-503H | B. I. Chemicals |
| (RG-501H):(RG-502H) blends* | B. I. Chemicals |
| (RG-501H):(PEG/PLGA)** | B. I. Chemicals |

*Polymer blends made by mixing 20:80 & 50:50 weight ratios of RG-501H and RG-502H
**80:20 (by weight) blend of PLGA (501H) and PLGA(501H):PEG(1000) AB block copolymer.

Using each of the polymers listed in Table 2, protein loaded microparticles could be effectively prepared.

EXAMPLE 3

This example describes the preparation of microparticles containing OB protein derivatives as well as other proteins. The preparation and evaluation procedures described in Example 1 were utilized to test the various proteins listed in Table 3 below.

TABLE 3

| Protein | Molecular Weight (Daltons) | Concentration: (mg/mL) | Formulation: |
| --- | --- | --- | --- |
| OB protein | 16,158 | 50–130 | 10 mM NaAcO, pH 4.8–8.0 |
|  |  | 80 | 10 mM NaAcO pH 4.8 + 10% Sucrose |
|  |  | 100 | Lyo Buffer[a] |
|  |  | 60 | Lipid Complexed[b] |

TABLE 3-continued

| Protein | Molecular Weight (Daltons) | Concentration: (mg/mL) | Formulation: |
| --- | --- | --- | --- |
| 20 kd PEG-OB protein | ~36,158 | 64–122 | 10 mM NaAcO, pH 4.8–8.0 |
| Succinylated OB protein | 16,258 | 60–80 | 10 mM NaPhos, pH 7.0–8.0 |
| G-CSF | 18,798 | 50–100 | 10 mM NaAcO, pH 4.8–8.0 |
|  |  | 60–100 | 10 mM NaAcO, pH 4.8–8.0 + 5–16% Sucrose |
|  |  | 55 | 1 mM NaCl, 10% Trehalose, pH 7.6 |
|  |  | 60 | Lipid Complexed[b] |
| BDNF | 13,513 | 45–120 | 100 mM NaPhos, pH 7 |
| IL-1ra | 17,258 | 100–200 | 10 mM NaCitrate, 140 mM NaCl, pH 6.5 |
| TNFbp | 18,278 | 105 | 10 mM NaPhos, 2% Gly, 1% Sucrose, pH 7 |
| BSA | 66,262 | 100 | 10 mM NaAcO, pH 4.8 |

[a]Lyophilization Buffer = 10 mg/mL Glycine, 5 mg/mL Sucrose, 10 mM glutamic acid, pH 4.5.
[b]Lipid complexed 30:1 mol. ratio DMPG or DCPG to protein in 20 mM NaAcO, pH 4.8.

With each of the proteins listed above, protein loaded microparticles were obtained, thus demonstrating the flexibility of the novel process of the present invention. And importantly, it is demonstrated that protein loaded microparticles can also be effectively prepared using different OB protein derivatives.

EXAMPLE 4

In this example, the effects of temperature on the freezing step and lyophilization step of the process of the present invention were evaluated. As relates to the freezing step (step 5), liquid nitrogen, −80° C. and −45° C. were tested. As relates to the lyophilization step (step 6), −80° C., −45° C., and −25° C. were tested. The procedure described in Example 1 was used to test the various temperatures and it was determined that the tested temperatures had very little effect on either step in the process.

EXAMPLE 5

In this example, different organic solvents were tested to dissolve the PLGA polymers in the methods of the present invention. The procedure described in Example 1 was repeated using ethyl acetate, methylene chloride. Each of the tested organic solvents were found to be effective in the methods of the present invention.

EXAMPLE 6

This example tested the ability of an active ingredient suspension to be used in the methods of the present invention. A 100 mg/mL, in 10 mM Tris, 50 µM Zinc chloride, pH 7.0, Zn/OB protein suspension (prepared as described in the Materials and Methods section below) was tested and evaluated as described in Example 1. It was demonstrated that the Zn/OB protein suspension could be effectively utilized to prepare microparticles according to the novel methods of the present invention.

EXAMPLE 7

This example tested the ability of a spray-dried protein, spray-dried IL-1ra, to be used in the methods of the present invention. A 150 mg spray-dried IL-1ra powder (prepared as described in the Materials and Methods section below) was tested and evaluated as described in Example 1. It was demonstrated that the spray-dried IL-1ra preparation could be effectively utilized to prepare microparticles according to the novel methods of the present invention.

EXAMPLE 8

In this example, the method described in Example 1 was modified such that 20 mM NaAcO, pH 4.8, was mixed initially with the polymer, resulting in the preparation of "blank" microparticles. 6 mg of blank microparticles was then diluted with 1 mL of BDNF (4.4 mg/mL in 0.1M sodium phosphate, pH 6.9) and the mixture incubated at 37° C. with shaking. After 2 hours, microparticles were isolated by centrifugation and the unbound protein fraction was determined by UV spectrophotometer. 1.76 mg of BDNF was bound to polymer to give 22% protein loading on the microparticles. In vitro release kinetics were then determined as described in Example 1. The % BDNF released over time is depicted in FIG. 7.

Materials and Methods

1. Preparation of Recombinant Methionyl Human OB Protein.

The present recombinant methionyl-human-OB protein may be prepared according to the above incorporated-by-reference PCT publication, WO 96/05309 at pages 151–159. For the present working examples, a human OB protein was used which has (as compared to the amino acid sequence at page 158) a lysine at position 35 instead of an arginine, and an isoleucine at position 74 instead of an isoleucine. Other recombinant human OB proteins may be prepared according to methods known generally in the art of expression of proteins using recombinant DNA technology.

2. Preparation of Spray Dried Recombinant IL-1ra.

The present spray dried recombinant IL-1ra protein was prepared by spray drying a 20 mg/mL IL-1ra solution, using a Buchi 190 mini spray dryer. The inlet and outlet temperatures during spray drying were 130° C. and 90° C., respectively. Feeding rate was 1–2 mL/min, and a spray-dried IL-1ra powder obtained.

3. Preparation of Recombinant Methionyl Succinylated Human OB Protein.

The present recombinant methionyl succinylated human OB protein was prepared by reaction of recombinant human OB protein at ~150 mg/mL in sodium phosphate buffer at pH 7.0 with a 3–7 molar excess of succinic anhydride at 4° C. for two hours. The reaction is quenched by addition of solid hydroxyl amine to a final concentration of 0.5M and pH 8.5. The reaction mixture is then dialyzed vs. 10 mM sodium phosphate, pH 7.0 and the mono-succinylated OB protein form separated from di- and poly-succinylated OB protein forms by ion exchange chromatography.

3. Preparation of Zinc Derivatized Recombinant Methionyl Human OB Protein Suspension.

The present zinc derivatized recombinant methionyl human OB protein suspension was prepared by taking a 752 $\mu$l sample of recombinant human OB protein at 133 mg/mL in 1 mM HCl and adding 48 $\mu$l water, followed by 100 $\mu$l of 500 $\mu$M zinc chloride, followed by 100 $\mu$l of 1M TRIS, pH 8.5. There is an immediate Zn/OB protein precipitate that will rapidly fall out of solution at room temperature, but which can be readily resuspended.

While the present invention has been described in terms of certain preferred embodiments, it is understood that variations and modifications will occur to those skilled in the art. Therefore, it is intended that the appended claims cover all such equivalent variations which come within the scope of the invention as claimed.

I claim:

1. A method for making a composition comprising an active ingredient contained within polymeric microparticles, wherein a mixture of the active ingredient and the polymer are dispersed within a continuous phase, and the resulting dispersion is directly lyophilized to remove the water and organic solvents and form said microparticles.

2. A method according to claim 1 wherein said continuous phase is aqueous or organic.

3. A method according to claim 1 wherein the active ingredient-polymer mixture is obtained by dispersing an aqueous solution of the active ingredient in a second, non-aqueous phase containing the polymer, prior to addition to the continuous phase.

4. A method according to claim 1 wherein the active ingredient-polymer mixture is obtained by dissolving both components in a non-aqueous solvent prior to addition to the continuous phase.

5. A method according to claim 1 wherein the active ingredient is present as a dispersion of solid particles in a non-aqueous solution of the polymer, which is then added to the continuous phase.

6. A method according to claim 1, wherein said active ingredient is omitted from said mixture, thereby producing blank polymeric microparticles.

7. A method according to claim 6 further comprising active ingredient being loaded onto said blank polymeric microparticles by suspending said blank polymeric microparticles in active ingredient solution.

8. A method according to any of claims 1–7 wherein one or more excipients is combined with the active ingredient-polymer mixture prior to incorporation into the dispersion.

9. A method according to any of claims 1–7 wherein said continuous phase contains one or more excipients.

10. A method according to any of claims 1–7 wherein one or more excipients is mixed with the active ingredient and the same or a different excipient is present in the continuous phase.

11. A method according to claim 1 wherein said polymer is selected from the group consisting of biodegradable and/or biocompatible polymers.

12. A method according to claim 11 wherein said biodegradable polymers is selected from the group consisting of poly(lactide)s, poly(glycolide)s, poly(lactic acid)s, poly (glycolic acid)s, polyanhydrides, polyorthoesters, polyetheresters, polycaprolactone, polyesteramides, polycarbonate, polycyanoacrylate, polyurethanes, polyacrylate, blends and copolymers thereof.

13. A method according to claim 12 wherein said polymer is poly(lactide-co-glycolide)(PLGA), and wherein said polymer is dissolved in an organic solvent selected from the group consisting of chloroform, ethyl acetate, methylene chloride, acetonitrile, THF and acetone.

14. A method according to any of claims 1–10 wherein the active ingredient is selected from the group consisting of peptides, small molecules, sugars, carbohydrates, nucleic acids, lipids, and proteins.

15. A method according to claim 14 wherein said active ingredient is a protein selected from the group consisting of G-CSF, GM-CSF, M-CSF, MGDF, the interferons (alpha, beta, and gamma), interferon consensus, the interleukins (1–12), erythropoietin (EPO), fibroblast growth factor, TNF, TNFbp, IL-1ra, stem cell factor, nerve growth factor, GDNF, BDNF, NT3, platelet-derived growth factor, tumor growth factor (alpha, beta), OPG, and OB protein; or derivatives, analogs, fusions, conjugates, or chemically modified forms thereof.

16. A method according to claim 15 wherein said protein is OB protein, or a derivative, analog, fusion, conjugate, or chemically modified form thereof.

17. A method according to claim 16 wherein said modified form of OB protein is selected from the group consisting of Fc-OB protein fusion, succinylated-OB protein, and zinc derivatized OB protein.

18. A method according to claim 15 wherein said protein is G-CSF, or a derivative, analog, fusion, conjugate, or chemically modified form thereof.

19. A method according to claim 15 wherein said protein is BDNF, or a derivative, analog, fusion, conjugate, or chemically modified form thereof.

20. A pharmaceutical composition for the sustained-release of an active ingredient, said composition produced by the method of any of claims 1–15.

21. A pharmaceutical composition comprising OB protein, or a derivative, analog, fusion, conjugate, or chemically modified form thereof contained within a polymeric microparticle.

22. A pharmaceutical composition comprising G-CSF, or a derivative, analog, fusion, conjugate, or chemically modified form thereof contained within a polymeric microparticle.

23. A pharmaceutical composition comprising BDNF, or a derivative, analog, fusion, conjugate, or chemically modified form thereof contained within a polymeric microparticle.

* * * * *

UNITED STATES PATENT AND TRADEMARK OFFICE
CERTIFICATE OF CORRECTION

PATENT NO. : 6,020,004
DATED : February 1, 2000
INVENTOR(S) : Subodh, Shah

It is certified that error appears in the above-identified patent and that said Letters Patent is hereby corrected as shown below:

Column 5, line 19: Change "*Nature* 3:425-432" to -- *Nature* 372:425-432 --.

Signed and Sealed this

Third Day of April, 2001

Attest:

NICHOLAS P. GODICI

*Attesting Officer*     *Acting Director of the United States Patent and Trademark Office*